United States Patent
Lian et al.

(10) Patent No.: US 9,050,013 B2
(45) Date of Patent: Jun. 9, 2015

(54) DEVICE AND METHOD FOR FUSION BEAT DETECTION

(71) Applicant: BIOTRONIK SE & CO. KG, Berlin (DE)

(72) Inventors: Jie Lian, Beaverton, OR (US); Dirk Muessig, West Linn, OR (US)

(73) Assignee: Biotronik SE & Co. KG, Berlin (DE)

( * ) Notice: Subject to any disclaimer, the term of this patent is extended or adjusted under 35 U.S.C. 154(b) by 17 days.

(21) Appl. No.: 14/095,736

(22) Filed: Dec. 3, 2013

(65) Prior Publication Data

US 2014/0207013 A1 Jul. 24, 2014

Related U.S. Application Data

(60) Provisional application No. 61/754,982, filed on Jan. 22, 2013.

(51) Int. Cl.
*A61B 5/0452* (2006.01)
*A61N 1/37* (2006.01)
*A61B 5/0432* (2006.01)

(52) U.S. Cl.
CPC .......... *A61B 5/04525* (2013.01); *A61N 1/3702* (2013.01); *A61N 1/3712* (2013.01); *A61B 5/0432* (2013.01); *A61B 5/0452* (2013.01)

(58) Field of Classification Search
CPC ............. A61B 5/0452; A61B 5/04525; A61N 1/3702; A61N 1/3712
USPC ................................. 600/513, 516, 517, 523
See application file for complete search history.

(56) References Cited

U.S. PATENT DOCUMENTS

| | | | |
|---|---|---|---|
| 6,904,321 | B1 | 6/2005 | Bornzin et al. |
| 6,928,326 | B1 | 8/2005 | Levine |
| 6,950,704 | B1 | 9/2005 | Bradley |
| 7,006,869 | B2 | 2/2006 | Bradley |

(Continued)

FOREIGN PATENT DOCUMENTS

| | | |
|---|---|---|
| EP | 1291038 | 3/2003 |
| WO | 01/17608 | 3/2001 |

OTHER PUBLICATIONS

European Search Report issued for EP Appl. No. 14151738.3, dated Mar. 20, 2014, 7 pages.

*Primary Examiner* — Christopher D Koharski
*Assistant Examiner* — Michael Carey
(74) *Attorney, Agent, or Firm* — ARC IP Law, PC; Joseph J. Mayo (57) ABSTRACT

A heart monitoring and/or therapy device for detecting and quantifying fusion beats, wherein the device includes an IEGM signal sensing channel that puts out a recorded IEGM signal and an evaluation unit operatively connected to the IEGM signal sensing channel that detects fusion beats. The evaluation unit comprises or is connected to a template memory including at least a first template electrogram signal and a second template electrogram signal. The evaluation unit compares the recorded IEGM signal with both, the first and the second template electrogram signal and determines at least a first degree of similarity reflecting the similarities between the recorded electrogram signal and the first template electrogram signal, and a second degree of similarity reflecting the similarities between the recorded electrogram signal and the second template electrogram signal. The evaluation unit then calculates a fusion index (FI) from the at least two degrees of similarity.

16 Claims, 6 Drawing Sheets

(56) References Cited

U.S. PATENT DOCUMENTS

| | | |
|---|---|---|
| 7,328,066 B1 | 2/2008 | Levine |
| 7,647,104 B1 | 1/2010 | Snell et al. |
| 7,765,004 B2 | 7/2010 | Stalsbert et al. |
| 7,899,520 B2 | 3/2011 | Lian et al. |
| 7,979,113 B2 | 7/2011 | Dong et al. |
| 8,082,028 B2 | 12/2011 | Lian et al. |
| 8,090,434 B2 | 1/2012 | Lian et al. |
| 2003/0093126 A1* | 5/2003 | Obel et al. ............ 607/27 |
| 2004/0127949 A1 | 7/2004 | Kim et al. |
| 2006/0247693 A1 | 11/2006 | Dong et al. |
| 2008/0275522 A1* | 11/2008 | Dong et al. ............ 607/28 |
| 2008/0294217 A1* | 11/2008 | Lian et al. ............ 607/28 |

* cited by examiner

DEVICE AND METHOD FOR FUSION BEAT DETECTION

This application claims the benefit of U.S. Provisional Patent Application 61/754,982, filed on 22 Jan. 2013, the specification of which is hereby incorporated herein by reference.

BACKGROUND OF THE INVENTION

1. Field of the Invention

At least one embodiment of the invention generally relates to a heart monitoring and/or therapy device that is configured to detect fusion beats.

2. Description of the Related Art

Typically, fusion beat represents the merging of two different cardiac excitation waves. For patients with implantable cardiac pacemakers or defibrillators, generally, fusion beat is often caused by the merging of intrinsic cardiac depolarization and the excitation wave generated by the pacing device that has generated a ventricular pace (VP).

Generally, a ventricular pace may cause a stimulated ventricular depolarization of the heart muscle cells and thus a contraction of the myocardium if the strength of the ventricular pace is above a stimulation threshold. Typically, such supra-threshold ventricular pace (ventricular stimulation pulse, VP) may capture the ventricular myocardium unless the cells of the ventricular myocardium are refractory. A sub-threshold ventricular pace will typically not cause capture.

In demand pacemakers, generally, ventricular paces (ventricular stimulation pulses) are only generated if the pacemaker does not detect a natural (intrinsic) depolarization and/or contraction of the myocardium within a certain time window. However, there is always a possibility that a ventricular pace is issued while there is also an intrinsic depolarization. The simultaneous occurrence of paced and intrinsic depolarization typically results in fusion beats.

Fusion beat recognition is generally important for implantable cardiac devices for several reasons. First, cardiac stimulation that leads to fusion, typically, may represent a waste of battery power. Second, fusion beat, typically, may disrupt the normal cardiac conduction and lead to inefficient myocardial contraction. Third, typically, for an implantable device that implements automatic pacing capture management based on analysis of evoked response (that is the electrogram resulting from a stimulated (paced) depolarization), fusion beat is undesired because it may distort the electrogram signal.

On the other hand, intentional fusion pacing (as opposed to unintended fusion pacing) has been proposed as an alternative pacing modality for cardiac resynchronization therapy (CRT). In heart failure (HF) patients with left bundle brunch block (LBBB) but with intact right-side AV conduction, generally, timing the left ventricular (LV) pacing to create electrical fusion with spontaneous right ventricular (RV) activation may lead to equivalent or better hemodynamic improvement compared to conventional biventricular (BiV) pacing.

Therefore, fusion beat detection generally poses a particular technical challenge for implantable cardiac devices. The cardiac excitation after a pacing pulse typically may take the form that varies between a completely captured one (no intrinsic component) to a completely intrinsic one (no capture component), and the range may be viewed as a continuous spectrum of fusion with varying degrees. The clinical term pseudo-fusion generally refers to the superimposition of an ineffectual pacing spike on an intrinsic waveform. Hence, pseudo-fusion is generally viewed as a special case of fusion that is close to the intrinsic side of the spectrum.

Knowing the degree of fusion can be valuable for cardiac rhythm management. For example, generally, right ventricular (RV) apical pacing causes non-physiological ventricular activation. Special algorithms have been developed to minimize the RV pacing. However, the RV pacing statistics (e.g. number and frequency of RV pacing) maintained by the pacemaker may be misleading: Patient A who has 20% RV pacing may have lower risk of pacing-induced HF than patient B who has only 10% RV pacing—if the RV paces in patient A are mainly fusion beats dominated by intrinsic activity, whereas the majority of RV paces in patient B are fully captured beats. In another example, to maximize the efficacy of CRT, generally, a common strategy is to maximize the percentage of BiV or LV pacing. However, the BiV or LV pacing percentage generally may not reflect the true effectiveness of CRT, because that metric could be inflated by fusion beats, which may be common during episodes of atrial fibrillation with intrinsic AV conduction.

Generally, several methods have been proposed for detection of fusion beats by extracting the morphological features of the intracardiac electrogram (IEGM) signal (e.g., signal peak, slope, duration, zero-crossings, area, etc.) and comparing them to those obtained from the captured and/or intrinsic IEGM templates.

For example, U.S. Pat. No. 6,950,704 entitled "Use of ER Signal Variability for Fusion Detection and Response in Ventricular and Atrial Autocapture Algorithms", and U.S. Pat. No. 7,006,869 entitled "Method and Device for Enhanced Capture Tracking By Discrimination of Fusion Beats", both issued to Bradley, appear to disclose wherein fusion beat detection is performed based on template matching. In particular, specific features (or feature statistics) may be extracted from the post-pacing electrical response, such as the paced depolarization integral, the maximum positive slope, etc. Capture (CAP) template and loss-of-capture (LOC) template may respectively be created by overdrive pacing with supra-threshold amplitude and sub-threshold amplitude, respectively. According to Bradley, a beat may be identified as fusion if the extracted features of the post-pacing electrical response do not correspond to those from either CAP template or LOC template. This approach has several limitations. First, selected features cannot fully characterize the morphology of the IEGM signal. Second, although the CAP template is generally stable, the LOC response may show great variations due to multiple factors, for example, the amplitude-dependent pacing artifact, the timing of intrinsic activity after the LOC pace, etc. Therefore, a stable LOC template may not be available.

U.S. Pat. No. 6,904,321 to Bornzin et al., entitled "System and Method of Identifying Fusion for Dual-Chamber Automatic Capture Stimulation Device", appears to disclose wherein the far-field signal present in the atrial channel is examined for evidence of a far-field R wave whenever the ventricular channel detects a LOC. According to Bornzin et al., if a far-field R wave is present, then fusion is confirmed. If a far-field R wave is absent, then LOC is confirmed. This method assumes (a) fusion beat is always accompanied by far-field R wave in atrial IEGM, and (b) far-field R wave is absent in case of LOC. However, either assumption may not be true. Depending on the degree of fusion and the sensitivity setting of the atrial channel, a fusion beat may not be accompanied by a far-field component in the atrial channel. Contrarily, after a non-capture ventricular pace, the intrinsic ventricular activity (either depolarization or repolarization) may be detected in the atrial channel.

U.S. Pat. No. 7,765,004 to Stalsbert et al., entitled "Methods and Systems for Managing Fusion and Noise In Cardiac Pacing Response Classification", appears to disclose a method to classify captured beats, fusion/pseudo-fusion beats, and intrinsic activation was disclosed based on examination of signal peaks in one or more detection windows after the pacing pulse. The method of Stalsbert et al. relies on the assumption that the captured, fusion, and intrinsic beat each has its own characteristic profile of peak amplitude and timing. This assumption is not true, in particular for the fusion and intrinsic beat, which may show different peak amplitude and have varying latency after the pacing pulse. A similar approach was disclosed in U.S. Pat. No. 7,979,113 to Dong et al., entitled "Multi Channel Approach to Capture Verification", disclosing wherein more than one channel are used for beat classification.

In U.S. Pat. No. 6,928,326 issued to Levine, entitled "Diagnosis of Fusion or Pseudofusion", fusion or pseudo-fusion beat detection may be performed in two sequential steps. After delivering a stimulus, the device first performs capture detection by examining the evoked response. If the device finds the stimulus did not result in capture, then it further uses morphology discrimination algorithm to compare one or more portions of the sensed IEGM to the corresponding portions of a template, which represents the intrinsic waveform. If an adequate match exists between the compared portions, then the beat is classified as fusion and/or pseudo-fusion. According to this approach, no fusion or pseudo-fusion beat detection is performed if capture is detected after the pace. However, a captured pace can still result in fusion beat. That is, the device can capture the local myocardium and sense the evoked response, but the paced waveform can later fuse with the conducted intrinsic waveform. Therefore, this approach can misclassify a fusion beat to a captured beat.

BRIEF SUMMARY OF THE INVENTION

One or more embodiments of the invention are related to a heart monitoring and/or therapy device with improved fusion beat detection. Objectives of the invention according to at least one embodiment of the invention include providing a heart monitoring and/or therapy device with a capability to quantify the degree of fusion should it occur, and providing a heart monitoring and/or therapy device with a novel feature to quantify the burden of fusion to facilitate cardiac rhythm management.

According to one or more embodiments of the invention, these objectives may be achieved by a heart monitoring or therapy device for detecting and quantifying fusion beats, wherein the device may include
    an IEGM signal sensing channel that may put out a recorded IEGM signal showing at least prominent ventricular components, and
    an evaluation unit operatively connected to said IEGM signal sensing channel and may detect and quantify fusion beats.

The evaluation unit, in embodiments of the invention, may include or may be connected to at least one template memory including at least a first template electrogram signal representing an intrinsic beat and a second template electrogram signal representing a captured (stimulated) beat. The evaluation unit, in at least one embodiment, may compare the recorded IEGM signal with both, the first and the second template electrogram signals and to determine at least two degrees of similarity for the recorded IEGM signal, wherein the at least two degrees of similarity may include:
    a first degree of similarity that may reflect the similarities between the recorded electrogram signal and the first template electrogram signal, and
    a second degree of similarity that may reflect the similarities between the recorded electrogram signal and the second template electrogram signal.

In one or more embodiments of the invention, the evaluation unit may calculate a fusion index (FI) from the at least two degrees of similarity.

Thus, the heart monitoring or therapy device of the invention, in at least one embodiment, may allow quantitatively measuring the degree of fusion. The device according to embodiments of the invention may provide for fusion beat quantification, to characterize the degree of fusion in a quantitative manner. Embodiments of the invention describe a novel method and apparatus for fusion beat detection and for quantifying the degree of fusion after pacing.

One or more embodiments of the invention may include implantable cardiac devices including pacemakers, defibrillators and cardioverters, which stimulate cardiac tissue electrically to control the patient's heart rhythm.

In at least one embodiment, the device may continuously monitor the IEGM signal, preferably from a far field sensing channel, on a beat-by-beat basis. The device, in at least one embodiment, may also maintain two waveform templates, which may be generated from the same far field sensing channel and may represent the characteristic morphology of fully captured beat and purely intrinsic activation, respectively. After the delivery of each pacing pulse, according to one or more embodiments of the invention, the device may sense the post-pace IEGM signal, and then may compare it to the two templates, respectively. The comparison may be based on correlation analysis of the whole waveform, not limited to the expected evoked response window or any portion of the signal complex. Preferably, in one or more embodiment, the adaptive signed correlation index (ASCI) may be used for the correlation analysis to measure the similarity between the sensed IEGM signal and the template signal. Therefore, in embodiments of the invention, for each paced beat, two ASCI values may be obtained by comparing the post-pace IEGM with the capture template and intrinsic template, respectively. A novel fusion index (FI) may be constructed from these two ASCI values. The degree of fusion, in at least one embodiment, may be quantitatively measured by FI: a fully captured beat has FI value close to 0 and an intrinsic beat has FI value close to 1. Fusion beat is detected if the associated FI value falls between the predefined upper and lower FI thresholds. Furthermore, new diagnostic metrics, such as the fusion burden, may be obtained by means of statistical analysis of the FI of all paces.

One or more embodiments of the invention may include a method for detecting and quantifying fusion beats including:
    providing a first template electrogram signal representing an intrinsic beat and a second template electrogram signal representing a captured (stimulated) beat,
    comparing a recorded IEGM signal with both, the first and the second template electrogram signal, and
    determining at least two degrees of similarity for the recorded IEGM signal, wherein the at least two degrees of similarity may include
        a first degree of similarity reflecting the similarities between the recorded electrogram signal and the first template electrogram signal, and
        a second degree of similarity reflecting the similarities between the recorded electrogram signal and the second template electrogram signal, and calculating a fusion index FI from the at least two degrees of similarity.

Embodiments of the invention provide a novel method and system for fusion beat detection and quantification. Embodiments include at least the following unique advantages:

At least one embodiment of the invention may use far-field IEGM for morphological analysis. Near field IEGM may not reveal morphological features associated with fusion because it may only see the pacing induced activity that is close to the pacing electrodes, but not sense the intrinsic activity that may cause fusion in a location farther away from the pacing electrodes.

By way of one or more embodiments, IEGM morphology may independently be compared with both a capture template and an intrinsic template. Even if the device confirms the pacing captured the myocardium (e.g. the evoked response morphology has sufficient similarity to the capture template), in at least one embodiment, fusion may still occur with a certain delay. Therefore, if the comparison of IEGM morphology with intrinsic template is dependent on the result of capture detection, in embodiments of the invention, false negatives may occur because several fusion beats may be misclassified as captured beats.

Embodiments of the invention may evaluate the morphological similarity between IEGM and templates based on correlation analysis of the whole waveform, not limited to specific morphological features (e.g. slope, peak amplitude, zero-crossing, etc.) or partial segment of the waveform. This may lead to more accurate assessment of the morphological similarity between signals.

At least one embodiment of the invention may include a method to quantify the degree of fusion. The proposed fusion index (FI) may be a normalized value that ranges from 0 to 1, covering a continuous spectrum of pacing effect ranging from completely capture (no intrinsic component) to purely intrinsic (no capture component), and with varying degrees of fusion in between.

Using accurate fusion beat detection and fusion quantification, at least one embodiment of the invention may provide new statistical information (such as fusion beat percentage and fusion burden) that may be used to facilitate cardiac rhythm management. Therefore, embodiments of the invention may lead to a novel diagnostic feature for cardiac rhythm management (CRM) products.

According to one or more embodiments of the invention, the evaluation unit may compare, for each cardiac cycle, the recorded IEGM signal to said first and said second template electrogram signal and may yield two adaptive signed correlation index (ASCI) values ($ASCI_{cap}$ and $ASCI_{int}$), respectively.

Preferably, in at least one embodiment, the evaluation unit may determine each adaptive signed correlation index $ASCI_{cap}$ and $ASCI_{int}$, respectively, by trichotomizing each recorded IEGM signal based on three signal subspaces, then may calculate a signed correlation of the trichotomized vectors.

According to at least one embodiment, the evaluation unit may normalize the adaptive signed correlation index (ASCI) values in a range from −1 to +1.

In at least one embodiment, the evaluation unit may determine an evidence of non-capture (EN), and an evidence of intrinsic (EI) and to calculate the fusion index (FI) therefrom.

In one or more embodiments, the evaluation unit may determine the evidence of non-capture (EN) as follows:

$$EN = \begin{cases} 0 & 1 - ASCI_{cap} < \Delta \\ 1 & ASCI_{cap} < 0 \\ 1 - ASCI_{cap} & \text{others} \end{cases}$$

wherein, $\Delta$ may be a predefined capture tolerance, preferably in the range between 0 and 0.30.

Also in one or more embodiments, the evaluation unit may determine the evidence of intrinsic (EI) as follows:

$$EI = \frac{1 + ASCI_{int}}{2}$$

Preferably, in at least one embodiment of the invention, the evaluation unit may determine the fusion index FI as a product of EN and EI, that is, as:

$$FI = EN \times EI$$

wherein the fusion index preferably is a normalized index ranging from 0 to 1.

According to at least one embodiment, the IEGM signal sensing channel may be a far field sensing channel that may show prominent ventricular components including QRS complexes and T waves on a beat-by-beat basis.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
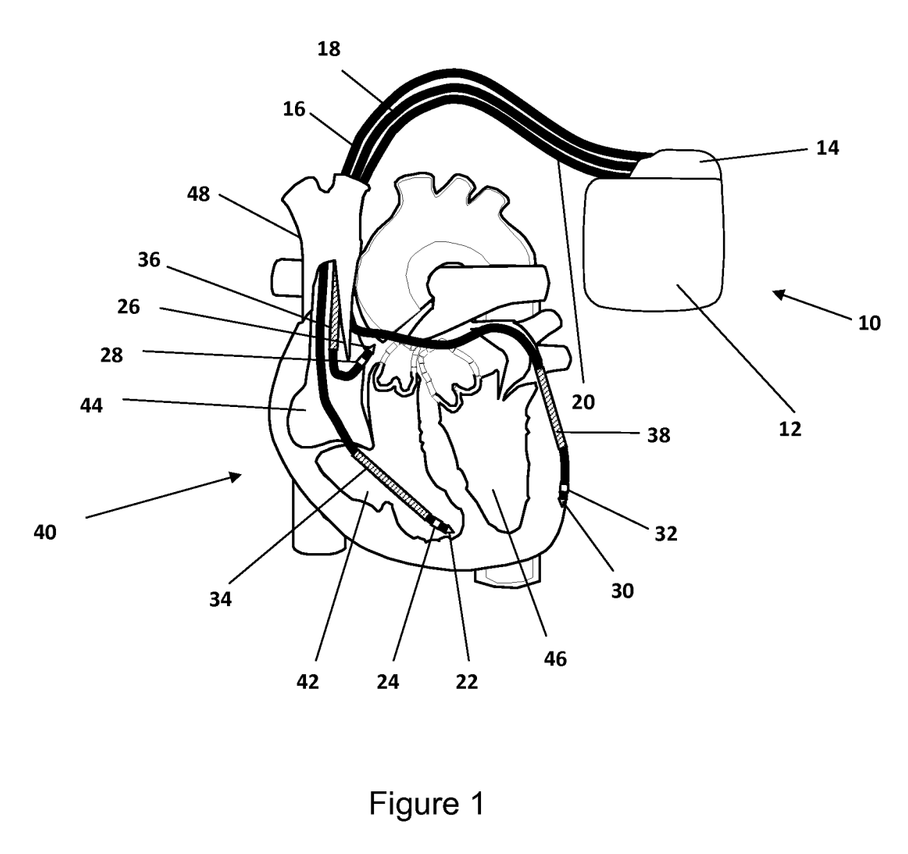
FIG. 1 shows a schematic illustration of an ICD system according to one or more embodiments of the invention.

FIG. 1 shows a schematic illustration of an ICD system. As shown in FIG. 1, the device according to one or more embodiments includes a stimulator 10 including a housing or case 12 and a header 14.

In at least one embodiment of the invention, the heart stimulator 10 may be connected to three electrode leads, namely a right ventricular electrode lead 16, a right atrial electrode lead 18 and a left ventricular electrode lead 20.

Figure 2:
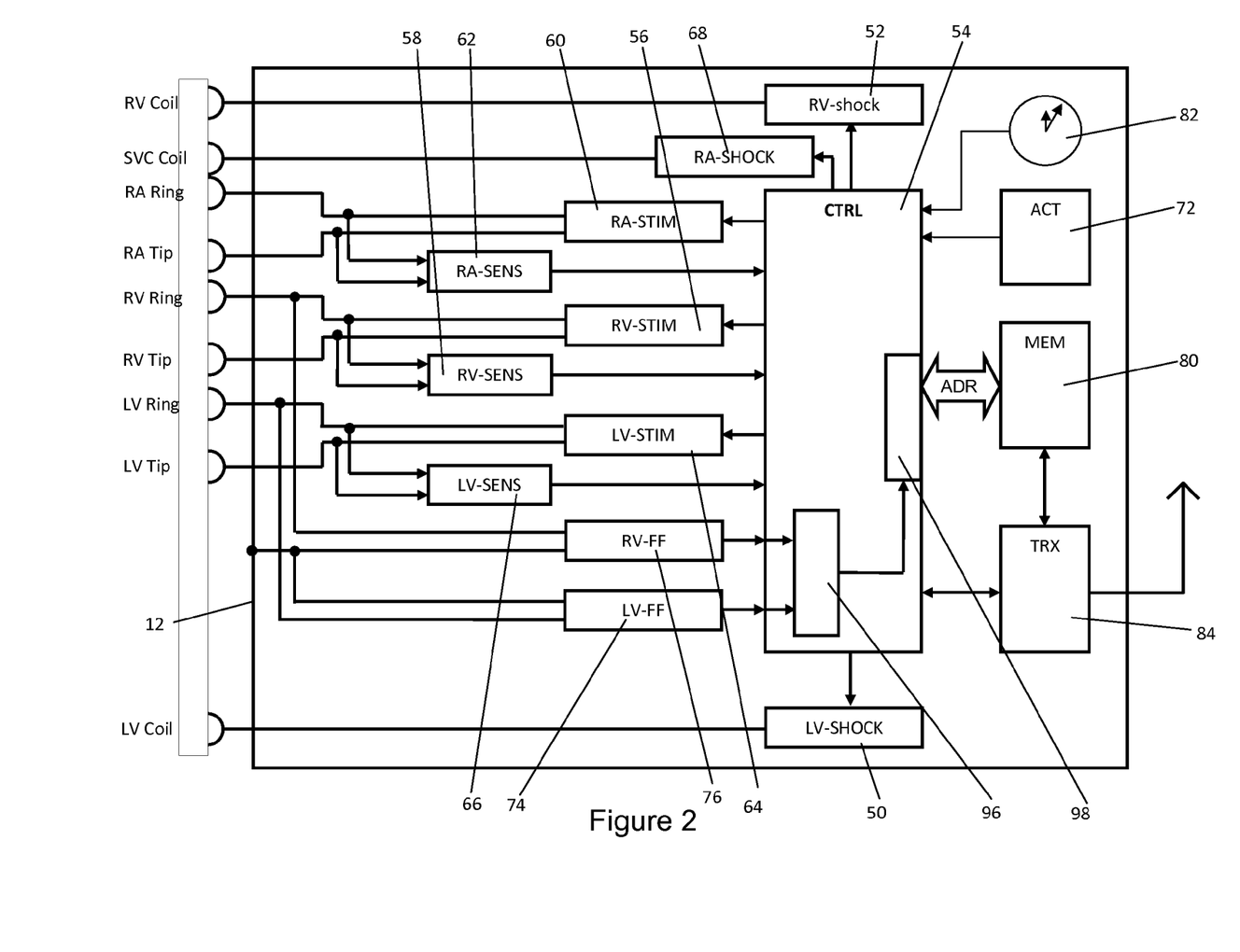
FIG. 2 shows an architectural view of an ICD system according to one or more embodiments of the invention.

FIGS. 1 and 2, according to embodiments of the invention, illustrate the pacing system that includes a heart stimulator 10 and the connected leads 16, 18, 20. The right atrial electrode lead 18, in at least one embodiment, may include a distal right atrial tip electrode 26 (RA-tip) at the distal end of right atrial electrode lead 18 and a proximal right atrial ring electrode 28 (RA-ring), as well as a superior vena cava coil electrode 36 (SVC-coil) that may include a large surface area.

The right ventricular electrode lead 16, in one or more embodiments, may include a distal right ventricular tip electrode 22 (RV-tip) at the distal end of right ventricular electrode lead 16 and a proximal right ventricular ring electrode 24 (RV-ring), as well as a right ventricular defibrillation coil electrode 34 (RV-coil) that may include a large surface area.

Similarly, in one or more embodiments, the left ventricular (LV) lead may include a distal left ventricular tip electrode 30 (LV-tip) and a proximal left ventricular ring electrode 32 (LV-ring), as well as a defibrillation coil electrode 38 (LV-coil) that that may include a large surface area. The left ventricular electrode lead 20, in at least one embodiment, may pass trough the coronary sinus of heart 40. A typical electrode suitable for use with heart stimulator 10 may include an electrode lead Corox+UP/BB made by the applicant.

Each electrode and shock coil of electrode leads 16 to 20, in at least one embodiment of the invention, may be separately connected to an electric circuit enclosed by case 12 of heart stimulator 10 by way of electrical contacts of a plug (not shown) at the proximal end of each electrode lead 16 to 20 and corresponding contacts (not shown) in header 14 of heart stimulator 10.

FIG. 2 shows an architectural view of an ICD system according to one or more embodiments of the invention. SVC shock coil 36, in at least one embodiment, may be connected to right atrial shock generator 68 that may be controlled by a control unit 54 of heart stimulator 10.

Similarly, in one or more embodiments, right ventricular shock coil 34 may be connected to a right ventricular shock generator 52 that may be connected to control unit 54 and left ventricular shock coil 38 may be connected to a left ventricular shock generator 50 that may also be connected to control unit 54.

Right atrial tip electrode 26 and right atrial ring electrode 28, in at least one embodiment, may both be connected to a right atrial stimulation pulse generator 60 and a right atrial sensing stage 62, that in turn may both be connected to control unit 54.

Right atrial stimulation pulse generator 60, in one or more embodiments, may generate atrial stimulation pulses of sufficient strength to cause an excitation of atrial myocardium by an electrical pulse delivered via right atrial tip electrode 26 and right atrial ring electrode 28. Preferably, in embodiments of the invention, the right atrial stimulation pulse strength may be adapted to the stimulation threshold in the right atrium.

By way of one or more embodiments, right atrial sensing stage 58 may be adapted to pick up myocardial potentials indicating an intrinsic atrial excitation that corresponds to a natural atrial contraction. By way of right atrial sensing stage 58, in at least one embodiment, it is possible to stimulate the right atrium 44 of heart 40 in a demand mode, wherein a right atrial stimulation pulse may be inhibited if an intrinsic atrial event (intrinsic atrial excitation) is sensed by right atrial sensing stage 58 prior to expiration of an atrial escape interval.

In a similar manner, according to one or more embodiments, right ventricular ring electrode 24 and right ventricular tip electrode 22 maybe connected to a right ventricular stimulation pulse generator 56 and to a right ventricular sensing stage 58 that in turn may be connected to control unit 54. By way of right ventricular tip electrode 22, in at least one embodiment, right ventricular ring electrode 24, right ventricular stimulation generator 56 and right ventricular sensing stage 58, right ventricular stimulation pulses may be delivered in a demand mode to the right ventricle 42 of heart 40.

In the same way, in one or more embodiments of the invention, left ventricular tip electrode 30 and left ventricular ring electrode 32 may be connected to the left ventricular stimulation pulse generator 64 and the left ventricular sensing stage 66 that in turn may both be connected to control unit 52 and that may allow for stimulating a left ventricle 46 of heart 40.

Triggering and inhibition of delivery of stimulation pulses to the right atrium, the right ventricle or the left ventricle, according to embodiments of the invention, may be controlled by control unit 54. In at least one embodiments, the timing that schedules delivery of stimulation pulses, if needed, may be controlled by a number of intervals that at least partly may depend on a hemodynamic demand of a patient that may be sensed by means of an activity sensor 72 that may be connected to control unit 54. Activity sensor 72, in one or more embodiments, may allow for rate adaptive pacing, wherein a pacing rate (the rate of consecutive ventricular stimulation pulses for a duration of consecutive atrial stimulation pulses) may depend on a physiological demand of a patient that may be sensed by a way of activity sensor 72.

A clock 82, in at least one embodiment, may allow recording of events and signals in association with time stamps that may enable a synchronous evaluation of signals at a later point of time.

For the purpose of composition of a far-field right ventricular electrogram (RV EGM) and a far-field left-ventricular electrogram (LV EGM), in one or more embodiments of the invention, a far-field right ventricular electrogram recording unit 74 and a far-field left ventricular recording unit 76, respectively, may be provided. As examples, in embodiments of the invention, the far-field right ventricular electrogram recording unit 74 may be connected to a case electrode that is formed by at least an electrically conducting part of case 12 of the heart stimulator 10 and to the RV ring electrode 24. The far-field left ventricular recording unit 76 may also connected to the case electrode formed by a case 12 of heart stimulator 10 and to the left ventricular ring electrode 32. For example, the far field RV and LV IEGM may also be recorded by connecting different electrodes or combination of different sensing vectors.

By way of one or more embodiments, the near-field electrogram in the right ventricle 42 may be measured between the RV-tip electrode 22 and RV-ring electrode 24. In one or more embodiments, the far-field electrogram in the right ventricle 38 may be measured between the RV-coil electrode 34 and the device can 12. Alternatively, the far-field electrogram in the right ventricle 38 may be measured between the RV-ring electrode 24 and the device can 12.

Likewise, in at least one embodiment, the near-field electrogram in the left ventricle 48 may be measured between the LV-tip electrode 30 and LV-ring electrode 32. In one or more embodiments, the far-field electrogram in left ventricle may be measured between the LV-coil electrode 38 and the device can 12. Alternatively, the far-field electrogram in the left ventricle 48 may be measured between the LV-ring electrode 32 and the device can 12.

Preferably, in at least one embodiment of the invention, the far-field electrogram in the right ventricle and the left ventricle may be minimally filtered and have wide bandwidth, e.g., with lower corner frequency 4 Hz and high corner frequency 128 Hz, whereas the near-field electrograms in the right ventricle and the left ventricle may be filtered with narrower bandwidth, e.g., with lower corner frequency 18 Hz and high corner frequency 40 Hz. Accordingly, in one or more embodiments, right and left far-field ventricular recording units 74 and 76 may each include a band pass filter with lower corner frequency (eg. 4 Hz) and high corner frequency (eg. 128 Hz). Right ventricular sensing stage 58 and left ventricular sensing stage 66 for picking up near-field electrograms in the right ventricle and the left ventricle, in at least one embodiment, may each include band pass filters with narrower bandwidth, e.g. with lower corner frequency 18 Hz and high corner frequency 40 Hz.

In embodiments of the invention, ventricular pacing may be used as an example to illustrate the concept of fusion beat detection and quantification. It should be understood that the same concept may also be applicable to atrial fusion beat detection and quantification.

According to at least one embodiment, the device may continuously monitor the IEGM signal, preferably from a far field sensing channel that shows prominent ventricular components (i.e. the QRS complex and the T wave) on a beat-by-beat basis. As already pointed out above, FIGS. 1 and 2 show a three-chamber ICD system that may include a device can, an RA lead with tip and ring electrodes and the SVC coil electrode, an RV lead with tip and ring electrode and the RV coil electrode, and an LV lead with tip and ring electrode and the LV coil electrode. Far field sensing vectors may include, but not limited to, RV ring-Can, LV ring-Can, RV coil-Can, LV coil-Can, SVC coil-RV coil, RA ring-RV ring, etc. Far-field IEGM, in one or more embodiments, may also be obtained by combining multiple sensing channels, for example, by forming a composite signal using the RV ring-Can channel and the LV ring-Can channel to measure the electrical activities from both RV and LV chambers, as shown in FIG. 2, far field electrogram composition unit 96. According to FIG. 2, the far field sensing vectors that may be used are RV ring-Can and LV ring-Can.

For ventricular fusion beat detection and quantification, according to one or more embodiments, the device may maintain two waveform templates in memory 80, that may be generated from the same far field sensing channel and represent the characteristic morphology of fully captured beat and purely intrinsic activation, respectively.

The capture and intrinsic templates, in at least one embodiment, may be created during the initial calibration phase. Specifically, to create the capture template, the device may overdrive the ventricle (by programming sufficiently short AV delay to avoid ventricular fusion) with supra-threshold pacing amplitude for multiple cycles. The device may then evaluate the IEGM signal after each pace. If the post-pace IEGM shows consistent waveform morphology over these multiple cycles, according to one or more embodiments, then their average waveform (note: all IEGM signals may be aligned with the device generated pace marker) may be calculated and saved as the initial capture template. Preferably, in embodiments of the invention, the capture template may cover both the depolarization phase (QRS complex) and part of the repolarization phase (T wave).

To create the intrinsic template, in at least one embodiment, the device may program the device AV delay longer than the intrinsic AV conduction time to encourage antegrade ventricular depolarization. The device in one or more embodiments may collect multiple cycles of the conducted ventricular IEGM signal, which may then be aligned based on a predefined fiducial point, for example, the positive or negative peak, the maximum slope, etc. For each cycle, in at least one embodiment, the IEGM segment in a fixed window relative to the fiducial point may be selected. If the aligned IEGM segments over multiple cycles have similar morphology, then their average waveform may be calculated and saved as the initial intrinsic template.

According to embodiments of the invention, signal alignment may be achieved by locating and aligning with the central peak of the windowed absolute integral (WAI) signal. The WAI signal, in at least one embodiments, may be obtained by transforming the original IEGM signal through a series of signal processing steps that may include rectifying, windowing, and integrating. Mathematically, the WAI operation may be expressed as:

$$S_{out}(k) = \sum_{i=k-w+1}^{k} |S_{in}(i)|$$

where $S_{out}(k)$ is the k-th output sample, $S_{in}(k)$ is the k-th input sample, w is the window size. Conceptually, the WAI signal $S_{out}$ may be interpreted as the windowed power of the input signal $S_{in}$. The central peak of the WAI signal represents the peak power of the input signal complex, and its location may be used to align the input IEGM signal.

In one or more embodiments, after the initial template setup, the template may be fixed until the next template setup phase. In at least one embodiment, the device may be programmed to enable template running update, that is, the template waveform may be continuously updated on a beat-by-beat basis. Preferably, in one or more embodiments, only captured beat that has similar morphology to the capture template may be used to update the capture template, and only intrinsic beat that has similar morphology to the intrinsic template may be used to update the intrinsic template. By this means, the template waveform may be dynamically adjusted to reflect possibly chronic change of the capture and/or intrinsic waveform morphology.

For a complete description of the template creation and maintenance, including the method to assess the similarity of signal morphology, the reader is referred to U.S. Pat. No. 7,899,520, U.S. Pat. No. 8,082,028, and U.S. Pat. No. 8,090,434, all issued to Lian et al. and assigned to the present assignee, which are hereby incorporated by reference.

Figure 3:
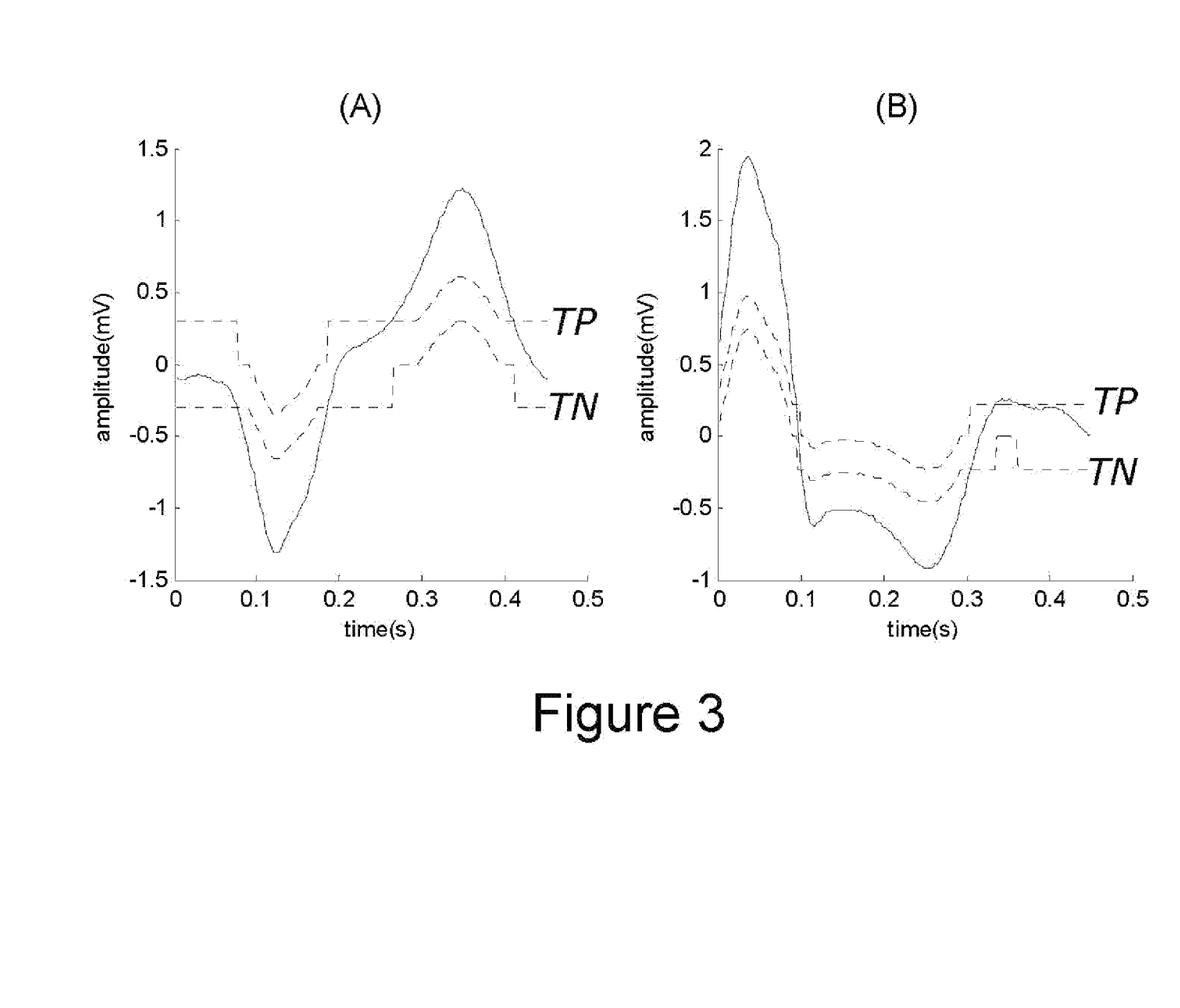
FIG. 3 shows an example of device generated (A) capture template and (B) intrinsic template according to one or more embodiments of the invention.

FIG. 3 shows an example of device generated (A) capture template and (B) intrinsic template according to one or more embodiments of the invention. As examples, FIG. 3 shows (A) a capture template waveform and (B) an intrinsic template waveform generated by the device. In addition, for each template waveform, in at least one embodiment, a positive threshold vector (TP) and a negative threshold vector (TN) are shown. These threshold vectors, which may be custom designed, divide the signal space into three non-overlapping subspaces. As taught in U.S. Pat. Nos. 7,899,520, 8,082,028, and 8,090,434, all issued to Lian et al. and assigned to the present assignee, the morphological similarity between two IEGM signals may be quantified by their adaptive signed correlation index (ASCI). The ASCI between two signals, in at least one embodiment of the invention, may be calculated by trichotomizing each signal based on the three signal subspaces, then calculating the signed correlation of the trichotomized vectors. The ASCI may be a normalized index ranging from −1 to +1. The ASCI between signals with similar morphology, in embodiments of the invention, approaches 1 due to more concordant sample pairs, whereas the ASCI between signals with different morphology may be lower or approaches −1 due to more nilcordant or discordant sample pairs. Compared to conventional correlation coefficients, in one or more embodiments, ASCI may have the dual advantage of low computational complexity and sensitivity to amplitude difference, thus making it particularly useful in applications designed for low-power embedded systems such as the implantable cardiac devices. On the other hand, it should be understood that other methods of measuring similarity between signals that may yield a normalized index, such as the Pearson's correlation coefficient, signed correlation coefficient, etc., may also be applied to evaluate the similarity between the post-pace IEGM and the capture and intrinsic template waveforms, and they are within the scope of this invention.

According to one or more embodiments, after the delivery of each ventricular pacing pulse, the device may sense the post-pace far field IEGM signal and then may compare it to the capture template and intrinsic template, respectively, by means of far field electrogram evaluation unit 98. As described above, the comparison is preferably based on ASCI, which measured the morphological similarity of the post-pace IEGM and two templates, respectively. Note that the morphological comparison may be based on the whole waveform, not limited to the expected evoked response window or any portion of the signal complex. Therefore, for each paced event, in at least one embodiment of the invention, two ASCI values may be calculated: $ASCI_{cap}$ and $ASCI_{int}$, which measure the morphological similarity between post-pace IEGM and the capture template, and between post-pace IEGM and the intrinsic template, respectively.

Figure 4:
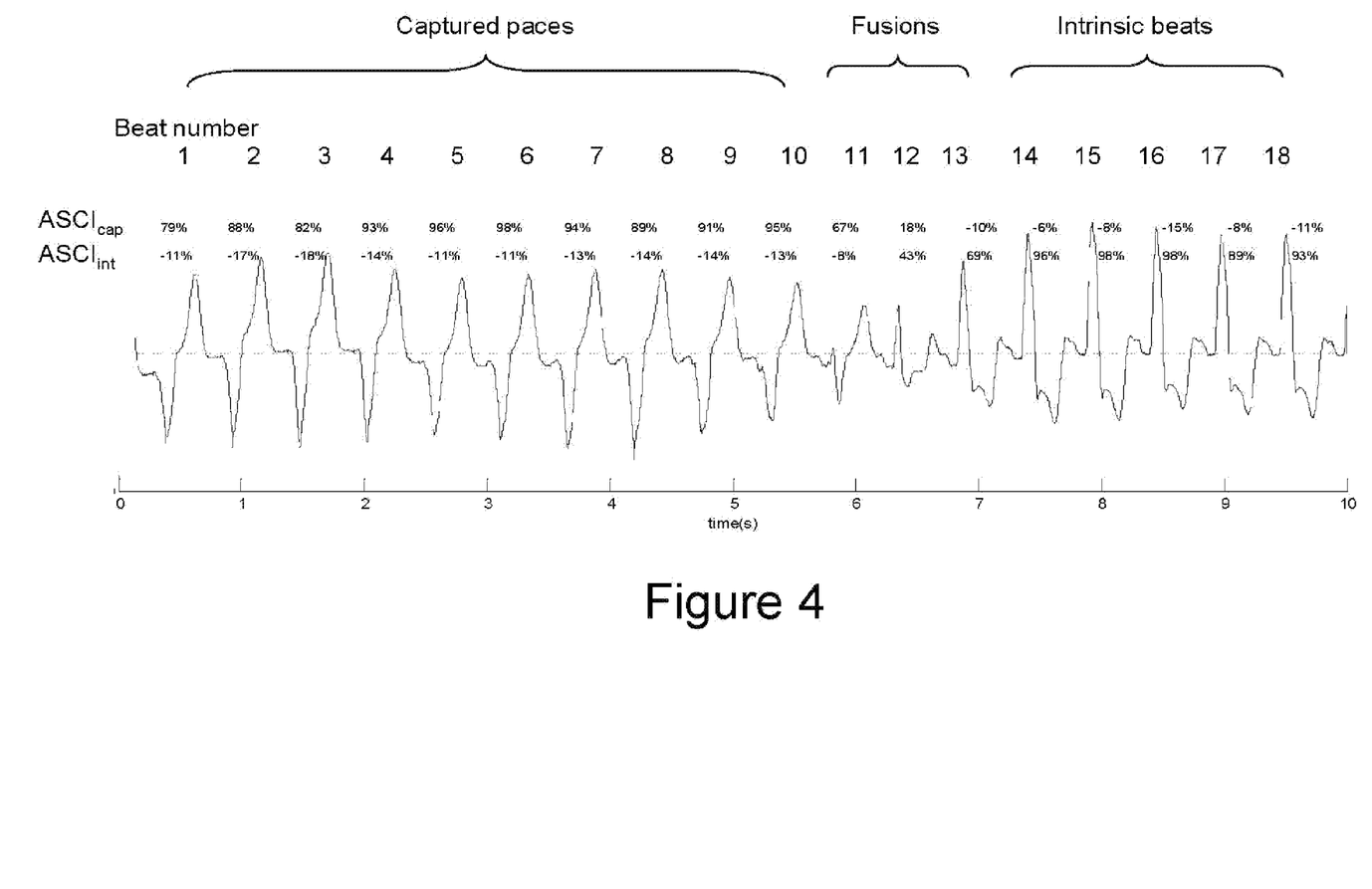
FIG. 4 shows a segment of IEGM consisting of capture, fusion, and intrinsic beats, according to one or more embodiments of the invention.

FIG. 4 shows a segment of IEGM consisting of capture, fusion, and intrinsic beats, according to one or more embodiments of the invention. As an example, FIG. 4 shows a segment of far-field IEGM consisting of capture, fusion, and intrinsic beats.

This segment shows 18 complete cardiac cycles, where each QRS complex is preceded by a ventricular pace (VP). The VP amplitude, in one or more embodiments, was gradually decreased from a supra-threshold value at the beginning to a sub-threshold value at the end of the segment. As a result, the first 10 cycles (beats 1-10) are captured beats with similar morphology to the capture template, the last 5 cycles (beats 14-18) are intrinsic beats with similar morphology to the intrinsic template, and the middle 3 cycles (beats 11-13) are fusion beats with mixed but varying degrees of morphological features from both templates. As described above, for each cardiac cycle, in at least one embodiment, the corresponding IEGM signal may be compared to the pre-calibrated capture template and intrinsic template, yielding two ASCI values ($ASCI_{cap}$ and $ASCI_{int}$), respectively.

Figure 5:
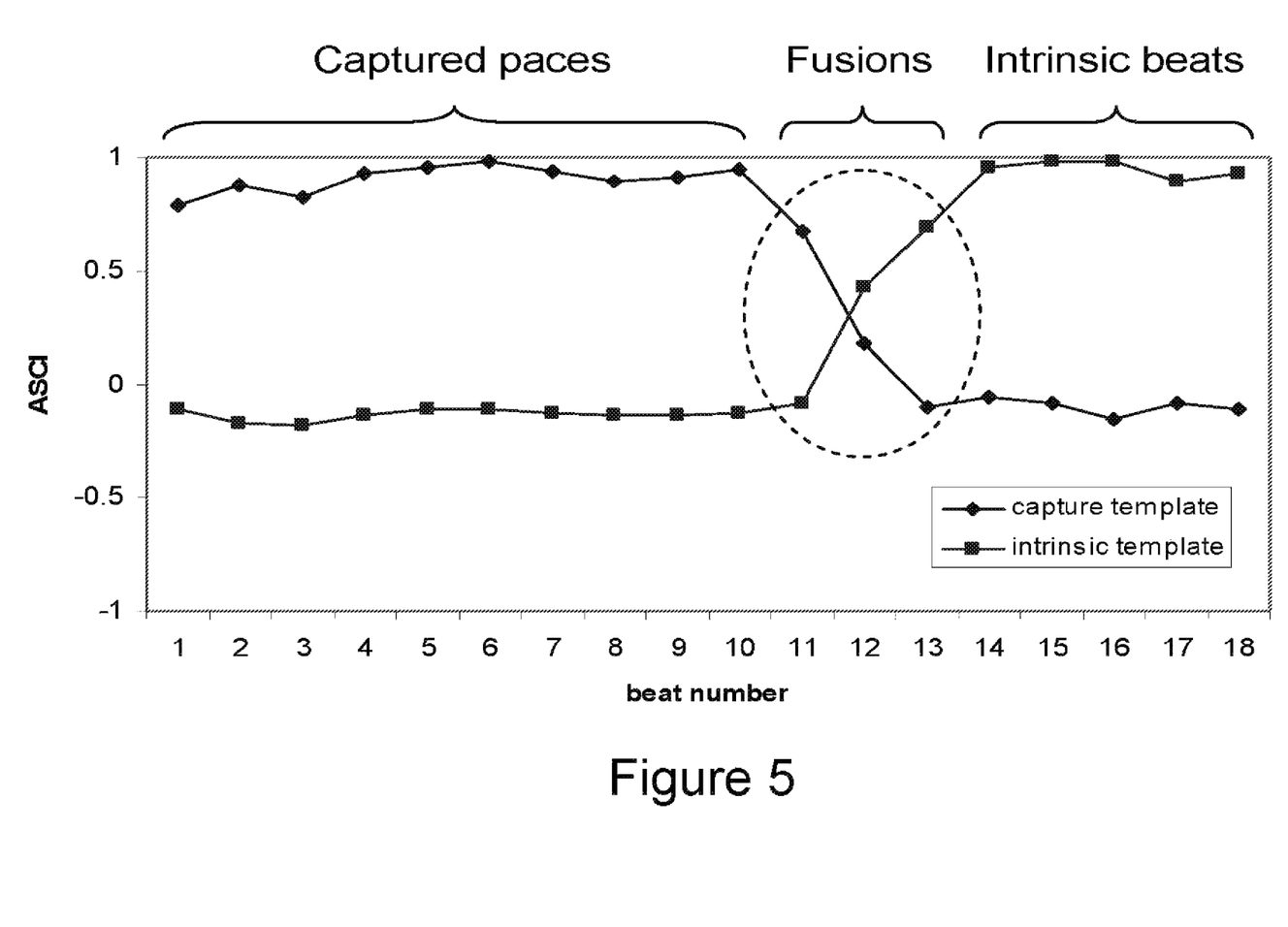
FIG. 5 shows calculated ASCI values corresponding to the 18 cycles shown in FIG. 4, according to one or more embodiments of the invention.

The ASCI values ($ASCI_{cap}$ and $ASCI_{int}$) corresponding to the 18 beats shown in FIG. 4, by way of one or more embodiments, may further be plotted in FIG. 5. FIG. 5 shows calculated ASCI values corresponding to the 18 cycles shown in FIG. 4, according to one or more embodiments of the invention. In embodiments of the invention, the captured beats (1-10) may be associated with high values of $ASCI_{cap}$ (all >0.75) and low values of $ASCI_{int}$ (all <0), and the intrinsic beats (14-18) may all be associated with high values of $ASCI_{int}$ (all >0.75) and low values of $ASCI_{cap}$ (all <0), whereas the fusion beats (11-13) may be associated with intermediate values of $ASCI_{cap}$ and/or $ASCI_{int}$.

Although beats 11-13 are all fusion beats, in one or more embodiments, the degree of fusion differs. As can be seen in FIG. 4, in at least one embodiment of the invention, fusion beat 11 may have more dominant morphological features of capture waveform, and fusion beat 13 may have more dominant morphological features of intrinsic waveform. On the other hand, fusion beat 12 may have intermediate level of morphological features associated with both capture and intrinsic waveforms, in one or more embodiments.

According to embodiments of the invention, a novel fusion index (FI) may be constructed by the far field electrogram evaluation unit 98 from the two ASCI values ($ASCI_{cap}$ and $ASCI_{int}$). The FI may be consisted of two components: evidence of non-capture (EN), and evidence of intrinsic (EI).

In one or more embodiments, the EN component is defined as:

$$EN = \begin{cases} 0 & 1 - ASCI_{cap} < \Delta \\ 1 & ASCI_{cap} < 0 \\ 1 - ASCI_{cap} & \text{others} \end{cases}$$

Here, $\Delta$ may be a predefined capture tolerance, preferably in the range between 0 and 0.30. For example, if $\Delta=0.25$ and $ASCI_{cap}=0.79$, then EN=0 according to above definition, implying that there is no evidence of non-capture. As the IEGM morphology more and more deviates from the capture template, in at least one embodiment, the $ASCI_{cap}$ may progressively decrease, and correspondingly EN may progressively increase toward the upper limit 1.

In at least one embodiment, the EI component may be defined as:

$$EI = \frac{1 + ASCI_{int}}{2}$$

Because $ASCI_{int}$ is within range [−1, 1], in one or more embodiments, EI may vary between 0 and 1. Evidently, as the IEGM morphology becomes more similar to the intrinsic template, the EI may progressively increase toward 1.

According to embodiments of the invention, the FI may be defined as the product of EN and EI, that is,

FI=EN×EI

Evidently, in at least one embodiment, FI may be a normalized index ranging from 0 to 1. This novel index may offer a quantitative means to measure the degree of fusion. A fully captured beat may have an FI value close to 0 and an intrinsic beat may have an FI value close to 1. The intermediate value of FI indicates fusion. Smaller FI indicates the fusion beat may have more capture component than intrinsic component. This occurs when the pacing induced wavefront has depolarized a relatively large portion of the ventricles before fusing with the intrinsic wavefront. On the other hand, in at least one embodiment, larger FI implies that the fusion beat may have more intrinsic component than capture component. This occurs when the intrinsic wavefront may have depolarized a relatively large portion of the ventricles before fusing with the pacing induced wavefront.

Figure 6:
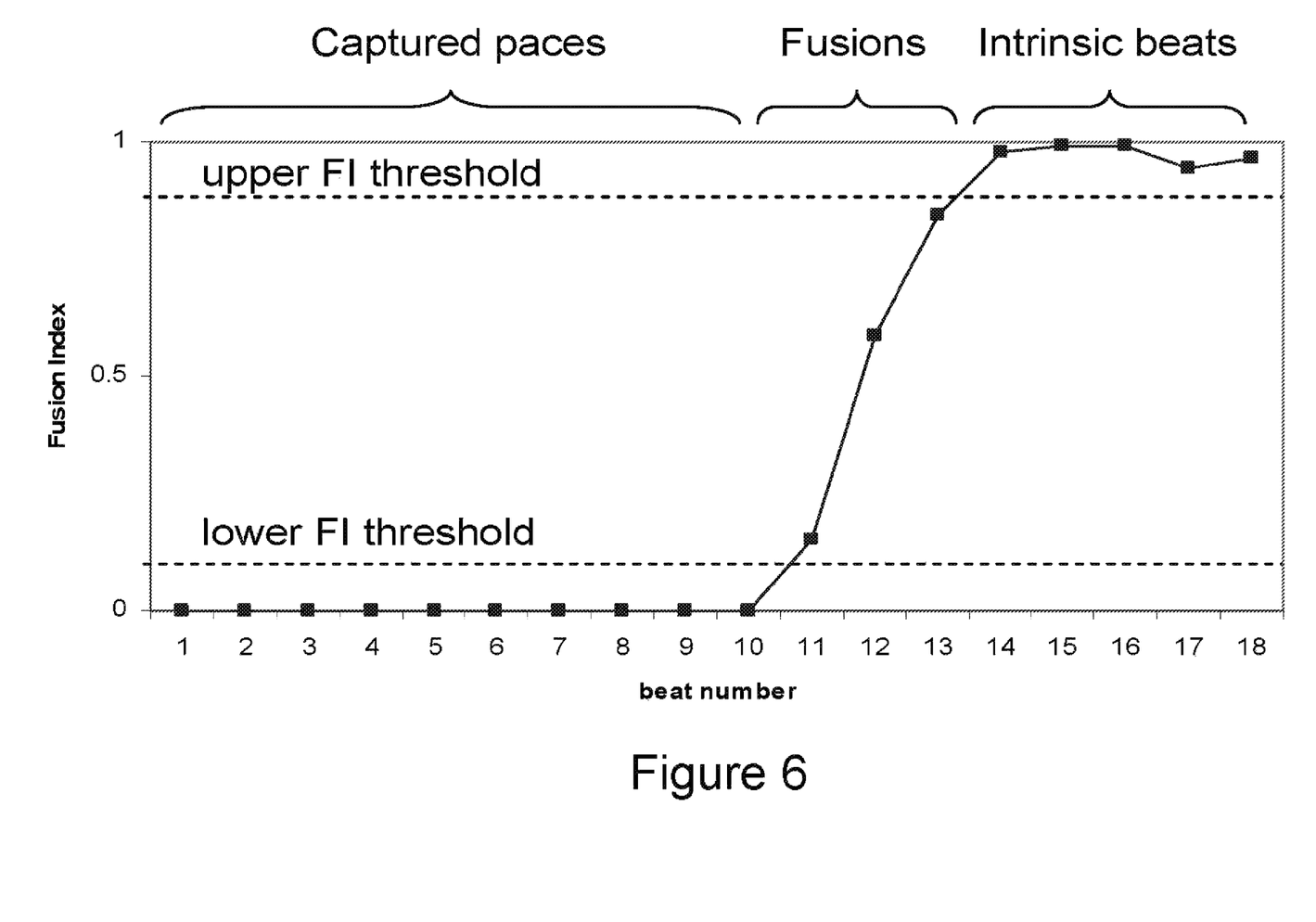
FIG. 6 shows calculated FI values corresponding to the 18 cycles shown in FIG. 4, according to one or more embodiments of the invention.

FIG. 6 shows calculated FI values corresponding to the 18 cycles shown in FIG. 4, according to one or more embodiments of the invention. For example, FIG. 6 plots the calculated FI values corresponding to the 18 cycles shown in FIG. 4. In this example, $\Delta$ may be set to 0.25. As shown in FIG. 6, the FI may be zero for all captured beats (1-10), and may be >0.90 for all intrinsic beats (14-18). Fusion beats (11, 12, 13) may have intermediate FI values (resp. 0.15, 0.59, 0.85).

According to at least one embodiment of the invention, fusion beat may be detected if the associated FI value falls between the predefined upper and lower FI thresholds. As illustrated in FIG. 6, according to at least one embodiment of the invention, the lower FI threshold defines a limit, below which the beat may be classified as a fully captured beat, and the upper FI threshold defines a limit, above which the beat may be classified as a purely intrinsic beat. In one or more embodiments, the lower FI threshold may be set to 0.25 and the lower FI threshold may be set to 0.90. Preferably, the upper and lower FI thresholds may be programmed by the user.

According to embodiments of the invention, new diagnostic metrics may be obtained by means of statistical analysis of the FI of all paces. One exemplary metric may be the percentage of fusion beats, which may be calculated as the ratio between the number of detected fusion beats and the total number of paces over a period of time (e.g. daily, monthly, etc). In another example, in at least one embodiment, the fusion burden may be defined as the sum of FI values for all paced beats over a period of time (e.g., daily, monthly, etc). Alternatively, in one or more embodiments, the fusion burden may be defined as a normalized metric by dividing the sum of FI values for all paced beats by the total number of paces over the period. These new metrics derived from fusion beat detection and quantification may provide a whole new dimension of diagnostic information for cardiac rhythm management. For example, a patient with an implanted CRT device may not respond to the CRT therapy if many LV paces result in fusion—despite nearly 100% BiV pacing. However, the new diagnostic metrics derived from fusion beat detection and fusion burden quantification may reveal the underlying problem, and may guide the physician to correct the issue and improve patient's outcome, for example, by programming a shorter device AV delay to minimize the fusion beats.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A heart monitoring or therapy device configure to detect and quantify fusion beats comprising
   an IEGM signal sensing channel configured to put a recorded IEGM signal showing at least prominent ventricular components; and
   an evaluation unit operatively connected to said IEGM signal sensing channel and configured to detect fusion beats,
   wherein said evaluation unit comprises or is connected to at least one template memory comprising at least a first template electrogram signal representing an intrinsic beat and a second template electrogram signal representing a captured beat, and
   wherein said evaluation unit is further configured to
      compare the recorded IEGM signal with both, said first and said second template electrogram signal and to determine at least two degrees of similarity for the recorded IEGM signal, wherein said at least two degrees of similarity comprise
         a first degree of similarity reflecting similarities between the recorded IEGM signal and the first template electrogram signal, and
         a second degree of similarity reflecting similarities between the recorded IEGM signal and the second template electrogram signal; and
   wherein said evaluation unit is further configured to
      calculate a fusion index (FI) from said at least two degrees of similarity;
      determine an evidence of non-capture (EN), and an evidence of intrinsic (EI) and calculate the fusion index (FI) therefrom;
      determine said evidence of intrinsic (EI) as follows:

$$EI = \frac{1 + ASCI_{int}}{2};$$

wherein $ASCI_{int}$ is a first adaptive signed correlation index value;
      determine the fusion index (FI) as a product of said EN and EI, that is, as:

FI=EN×EI;

determine diagnostic metrics from the fusion index (FI); and,
      enable said heart monitoring or therapy device to provide cardiac rhythm management based on said diagnostic metrics to control a patient's heart rhythm.

2. The device of claim 1, wherein said fusion index FI comprises a degree of fusion in a quantitative manner.

3. The device of claim 2, wherein said evaluation unit is further configured to compare, for each cardiac cycle, the recorded IEGM signal to said first and said second template electrogram signal, and to yield two adaptive signed correlation index (ASCI) values, wherein said two adaptive signed correlation index (ASCI) values Comprise $ASCI_{cap}$ and said $ASCI_{int}$, respectively.

4. The device of claim 3, wherein said evaluation unit is further configured to determine each of said adaptive signed correlation index $ASCI_{cap}$ and $ASCI_{int}$, respectively, through trichotomization of each recorded IEGM signal based on three signal subspaces, and through calculation of a signed correlation of trichotomized vectors.

5. The device of claim 4, wherein said evaluation unit is further configured to normalize the adaptive signed correlation index (ASCI) values in a range from ×1 to +1.

6. The device of claim 1, wherein said evaluation unit is further configured to determine said evidence of non-capture (EN) as follows:

$$EN = \begin{cases} 0 & 1 - ASCI_{cap} < \Delta \\ 1 & ASCI_{cap} < 0 \\ 1 - ASCI_{cap} & others \end{cases}$$

wherein, $\Delta$ is a predefined capture tolerance and $ASCI_{cap}$ is a second adaptive signed correlation index value.

7. The device of claim 6, wherein said predefined capture tolerance A is in a range between 0 and 0.30.

8. The device of claim 1, wherein said evaluation unit is further configured to calculate the fusion index (FI) as a normalized index ranging from 0 to 1.

9. The device of claim 1, wherein said IEGM signal sensing channel is a far field sensing channel that is configured to show prominent ventricular components including QRS complexes and T waves on a beat-by-beat basis.

10. The device of claim 1, wherein said device is an implantable pacemaker or an implantable cardioverter/defibrillator or a combination thereof.

11. A method of detecting and quantifying fusion beats, said method comprising:

providing a heart monitoring or therapy device comprising
an IEGM sensing channel configured to put out a recorded IEGM signal showing at least prominent ventricular components;
an evaluation unit operatively connected to said IEGM signal sensing channel and configured to detect fusion beats,
wherein said evaluation unit comprises or is connected to at least one template memory comprising a first template electrogram signal representing an intrinsic beat and a second template electrogram signal representing a captured beat;
wherein said evaluation unit performs processing comprising
comparing a recorded IEGM signal with both, the first and the second template electrogram signal,
determining at least two degrees of similarity for the recorded IEGM signal, wherein said at least two degrees of similarity comprise
a first degree of similarity reflecting similarities between the recorded IEGM signal and the first template electrogram signal, and
a second degree of similarity reflecting similarities between the recorded IEGM signal and the second template electrogram signal; and
calculates a fusion index (FI) from the at least two degrees of similarity,
determining an evidence of non-capture (EN), and an evidence of intrinsic (EI) and calculating the fusion index (FI) therefrom;
determining said evidence of intrinsic (EI) as follows:

$$EI = \frac{1 + ASCI_{int}}{2};$$

where $ASCI_{int}$ is an adaptive signed correlation index value;
determining the fusion index (FI) as a product of said EN and EI, that is, as:

FI=EN×EI determining diagnostic metrics from the fusion index (FI); and,
enabling said heart monitoring or therapy device to provide cardiac rhythm management based on said diagnostic metrics to control a patient's heart rhythm.

12. A heart monitoring or therapy device configured to detect and quantify fusion beats comprising
an IEGM signal sensing channel configured to put a recorded IEGM signal showing at least prominent ventricular components; and
an evaluation unit operatively connected to said IEGM signal sensing channel and configured to detect fusion beats,
wherein said evaluation unit comprises or is connected to at least one template memory comprising at least a first template electrogram signal representing an intrinsic beat and a second template electrogram signal representing a captured beat, and
wherein said evaluation unit is further configured to
compare the recorded IEGM signal with both, said first and said second template electrogram signal and to
determine at least two degrees of similarity for the recorded IEGM signal, wherein said at least two degrees of similarity comprise a first degree of similarity reflecting similarities between the recorded IEGM signal and the first template electrogram signal, and
a second degree of similarity reflecting similarities between the recorded IEGM signal and the second template electrogram signal; and
wherein said evaluation unit is further configured to
calculate a fusion index (FI) from said at least two degrees of similarity;
determine an evidence of non-capture (EN), and an evidence of intrinsic (EI) and calculate the fusion index (FI) therefrom;
determine said evidence of non-capture (EN) as follows:

$$EN = \begin{cases} 0 & 1 - ASCI_{cap} < \Delta \\ 1 & ASCI_{cap} < 0 \\ 1 - ASCI_{cap} & \text{others} \end{cases}$$

wherein, $\Delta$ is a predefined capture tolerance and $ASCI_{cap}$ is a first adaptive signed correlation index value;
determine diagnostic metrics from the fusion index (FI); and,
enable said heart monitoring or therapy device to provide cardiac rhythm management based on said diagnostic metrics to control a patient's heart rhythm.

13. The device of claim 12, wherein said predefined capture tolerance A is in a range between 0 and 0.30.

14. The device of claim 12, wherein said evaluation unit is further configured to determine said evidence of intrinsic (EI) as follows:

$$EI = \frac{1 + ASCI_{int}}{2},$$

wherein $ASCI_{int}$ is a second adaptive signed correlation index value.

15. The device of claim 12, wherein said evaluation unit is further configured to determine the fusion index (FI) as a product of EN and EI, that is, as:

FI=EN×EI.

16. A method of detecting and quantifying fusion beats, said method comprising:
providing a heart monitoring or therapy device comprising
an IEGM sensing channel configured to put out a recorded IEGM signal showing at least prominent ventricular components;
an evaluation unit operatively connected to said IEGM signal sensing channel and configured to detect fusion beats,
wherein said evaluation unit comprises or is connected to at least one template memory comprising a first template electrogram signal representing an intrinsic beat and a second template electrogram signal representing a captured beat;
wherein said evaluation unit performs processing comprising
comparing a recorded IEGM signal with both, the first and the second template electrogram signal,
determining at least two degrees of similarity for the recorded IEGM signal, wherein said at least two degrees of similarity comprise a first degree of similarity reflecting similarities between the recorded IEGM signal and the first template electrogram signal, and a second degree of similarity reflecting similarities between the recorded IEGM signal and the second template electrogram signal; and calculates a fusion index (FI) from the at least two degrees of similarity, determining an evidence of non-capture (EN), and an evidence of intrinsic (EI) and calculating the fusion index (FI) therefrom;

determining said evidence of non-capture (EN) as follows:

$$EN = \begin{cases} 0 & 1 - ASCI_{cap} < \Delta \\ 1 & ASCI_{cap} < 0 \\ 1 - ASCI_{cap} & \text{others} \end{cases}$$

wherein, $\Delta$ is a predefined capture tolerance and $ASCI_{cap}$ is an adaptive signed correlation index value;

determining diagnostic metrics from the fusion index (FI); and, enabling said heart monitoring or therapy device to provide cardiac rhythm management based on said diagnostic metrics to control a patient's heart rhythm.

\* \* \* \* \*